(12) United States Patent
Fujiwara et al.

(10) Patent No.: US 10,202,713 B2
(45) Date of Patent: Feb. 12, 2019

(54) TICKING

(71) Applicants: TEIJIN LIMITED, Osaka-shi, Osaka (JP); NITORI HOLDINGS CO., LTD., Sapporo-shi, Hokkaido (JP)

(72) Inventors: Norihisa Fujiwara, Osaka (JP); Ryo Yasumitsu, Osaka (JP)

(73) Assignees: TEIJIN FRONTIER CO., LTD., Osaka-shi (JP); NITORI HOLDINGS CO., LTD., Sapporo-shi (JP)

( * ) Notice: Subject to any disclaimer, the term of this patent is extended or adjusted under 35 U.S.C. 154(b) by 0 days.

(21) Appl. No.: 15/545,754

(22) PCT Filed: Mar. 17, 2016

(86) PCT No.: PCT/JP2016/059527
§ 371 (c)(1),
(2) Date: Jul. 24, 2017

(87) PCT Pub. No.: WO2016/153016
PCT Pub. Date: Sep. 29, 2016

(65) Prior Publication Data
US 2018/0016714 A1    Jan. 18, 2018

(30) Foreign Application Priority Data
Mar. 20, 2015 (JP) .............................. 2015-001317 U

(51) Int. Cl.
*D03D 13/00*    (2006.01)
*D03D 15/00*    (2006.01)
(Continued)

(52) U.S. Cl.
CPC ....... *D03D 15/0061* (2013.01); *A47C 27/002* (2013.01); *D03D 1/0017* (2013.01);
(Continued)

(58) Field of Classification Search
CPC .. D03D 13/008; D03D 15/00; D03D 15/0061; D03D 1/00
See application file for complete search history.

(56) References Cited

U.S. PATENT DOCUMENTS 3,889,305 A * 6/1975 Goldberg ............. A47C 31/001
5/698
4,525,409 A * 6/1985 Elesh .................. D06M 15/564
427/2.31
(Continued)

FOREIGN PATENT DOCUMENTS

JP    56-005687 A    1/1981
JP    2-216238 A    8/1990
(Continued)

OTHER PUBLICATIONS

Communication dated Feb. 28, 2018 from the Japanese Patent Office in counterpart application No. 2017-043960.
(Continued)

*Primary Examiner* — Bobby Muromoto, Jr.
(74) *Attorney, Agent, or Firm* — Sughrue Mion, PLLC

(57) ABSTRACT

Ticking having excellent flexibility is described. A woven fabric is obtained by using a multifilament having a monofilament fineness of not more than 0.5 dtex, the number of filaments of 100 or more and a total fineness of not more than 50 dtex and used as ticking. The woven fabric can be made of a polyester.

2 Claims, 1 Drawing Sheet

(51) Int. Cl.
    *A47C 27/00*     (2006.01)
    *D03D 1/00*     (2006.01)
    *A47G 9/02*     (2006.01)
    *A41D 3/00*     (2006.01)
    *A41D 13/00*     (2006.01)
    *A41D 31/00*     (2006.01)
    *A47G 9/08*     (2006.01)
    *B68G 7/05*     (2006.01)

(52) U.S. Cl.
    CPC ............ *D03D 13/008* (2013.01); *A41D 3/00* (2013.01); *A41D 13/0015* (2013.01); *A41D 31/0011* (2013.01); *A41D 2500/20* (2013.01); *A47G 9/02* (2013.01); *A47G 9/0261* (2013.01); *A47G 9/08* (2013.01); *B68G 7/05* (2013.01); *D10B 2503/06* (2013.01)

(56) References Cited

U.S. PATENT DOCUMENTS

| | | | | |
|---|---|---|---|---|
| 5,659,911 | A * | 8/1997 | Kirkbride | A47G 9/10 428/401 |
| 2003/0026987 | A1 * | 2/2003 | Ahn | B68G 1/00 428/375 |
| 2003/0170453 | A1 * | 9/2003 | Foss | A01N 57/16 428/373 |
| 2005/0118919 | A1 * | 6/2005 | Link | D04H 1/46 442/414 |
| 2011/0033687 | A1 * | 2/2011 | Deguchi | D03D 1/0041 428/219 |
| 2013/0177753 | A1 * | 7/2013 | Ukuma | D03D 13/008 428/219 |

FOREIGN PATENT DOCUMENTS

| | | |
|---|---|---|
| JP | 2004-204365 A | 7/2004 |
| JP | 2004-211268 A | 7/2004 |
| JP | 2004-270097 A | 9/2004 |
| JP | 2005-097817 A | 4/2005 |
| JP | 2005-179847 A | 7/2005 |
| JP | 3886525 B2 | 2/2007 |
| JP | 2009-091694 A | 4/2009 |
| JP | 2012-012739 A | 1/2012 |
| JP | 2015-001025 A | 1/2012 |
| JP | 5432139 B2 | 3/2014 |
| JP | 2014-205933 A | 10/2014 |
| WO | 2012/067053 A1 | 5/2012 |

OTHER PUBLICATIONS

International Search Report for PCT/JP2016/059527, dated Jun. 7, 2016 (PCT/ISA/210).
Translation of the International Preliminary Report on Patentability dated Oct. 5, 2017, in counterpart International Application No. PCT/JP2016/059527.
Communication dated Jun. 7, 2018 from the Japanese Patent Office in counterpart Application No. 2017-43960.

* cited by examiner

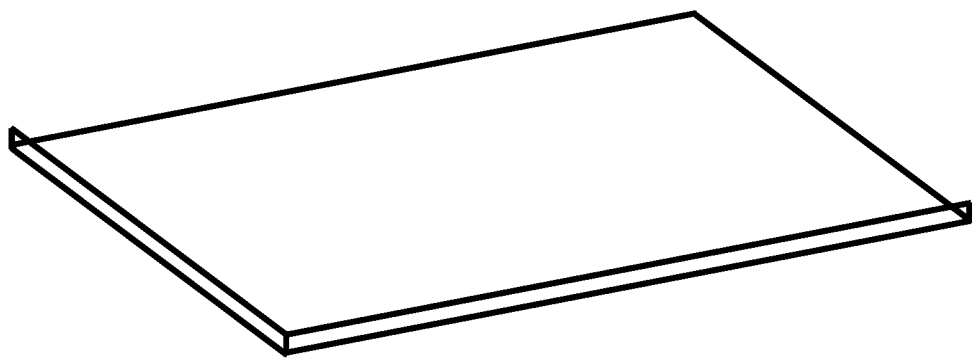

TICKING

CROSS REFERENCE TO RELATED APPLICATIONS

This application is a National Stage of International Application No. PCT/JP2016/059527 filed Mar. 17, 2016 (claiming priority based on Japanese Utility Model Application No. 2015-001317, filed Mar. 20, 2015), the contents of which are incorporated herein by reference in their entirety.

TECHNICAL FIELD

The present invention relates to ticking having excellent flexibility.

BACKGROUND ART

Heretofore, textile products comprising ticking and an inner material (such as inner cotton or down), such as down jackets, jackets stuffed with cotton, heavy winter clothing, sleeping bags, futons stuffed with cotton and down quilts have been widely used. The term "ticking" means cloth wrapping an inner material. As the above ticking, a woven fabric having low air permeability is generally used to prevent the inner material from protruding therefrom (refer, for example, to Patent Document 1).

However, the woven fabric having low air permeability has a problem that it is inferior in flexibility.
(Patent Document 1) JP-A 2012-12739

DISCLOSURE OF THE INVENTION

It is an object of the present invention which was made in view of the above background to provide ticking having excellent flexibility.

The inventors of the present invention conducted intensive studies to attain the above object and found that ticking having excellent flexibility is obtained by producing a woven fabric with a multifilament having a small monofilament fineness, a large number of filaments and a small total fineness and constituting ticking with this woven fabric. They conducted further intensive studies to arrive at the present invention.

Thus, according to the present invention, there is provided "ticking composed of a woven fabric containing a multifilament having a monofilament fineness of not more than 0.5 dtex, the number of filaments of 100 or more and a total fineness of not more than 50 dtex."

The above woven fabric is preferably composed of only the above multifilament. Further, the above multifilament is preferably formed of a polyester. The above woven fabric preferably has a cover factor (CF) defined by the following equation of not less than 1,200.

$$CF=(DWp/1.1)^{1/2} \times MWp + (DWf/1.1)^{1/2} \times MWf$$

[DWp is the total fineness (dtex) of warps, MWp is the weaving density of warps (number of warps/2.54 cm), DWf is the total fineness (dtex) of wefts, and MWf is the weaving density of wefts (number of wefts/2.54 cm)

It is preferred that the above woven fabric should be subjected to water absorption finish and/or calender finish. It is also preferred that the ticking should be futon ticking.

BRIEF DESCRIPTION OF THE DRAWINGS

FIG. 1 is a schematic diagram of the ticking of the present invention.

BEST MODE FOR CARRYING OUT THE INVENTION

While modes for carrying out the present invention will be detailed hereinbelow, it is to be understood that the present invention is not limited by these. To begin with, it is important that the multifilament contained in the woven fabric should have a monofilament fineness of not more than 0.5 dtex (preferably 0.000001 to 0.5 dtex), the number of filaments of 100 or more (preferably 100 to 10,000 filaments) and a total fineness of not more than 50 dtex (preferably 20 to 50 dtex, particularly preferably 20 to 35 dtex). When the above multifilament does not satisfy the above requirements, ticking having excellent flexibility may not be obtained disadvantageously. The above multifilament may be a super fine fiber having a monofilament diameter of not more than 1,000 nm, called "nanofiber".

It is important the above multifilament should be a long fiber. Spun yarn made of a short fiber is not preferred as the inner material may protrude due to a large space between fabric textures. The sectional form of the monofilament is not particularly limited and may be circular, triangular, flat, constricted flat, hollow or other known form.

The polymer forming the above multifilament is not particularly limited but preferably a polyester-based polymer. Preferred examples of the polyester-based polymer include polyethylene terephthalate, polytrimethylene terephthalate, polybutylene terephthalate, polylactic acid, stereocomplex polylactic acid and polyesters containing a third component. The polyester may be a material recycled or chemically recycled polyester, or polyethylene terephthalate obtained by using a monomer component obtained from biomass, that is, a material derived from organisms as described in JP-A 2009-091694. Further, polyesters obtained by using a catalyst containing a specific phosphorus compound and a specific titanium compound as described in JP-A 2004-270097 and JP-A 2004-211268 may also be used. One or more out of a delustering agent, pore forming agent, cationic dye dyeable agent, coloring inhibitor, thermal stabilizer, fluorescent brightener, coloring agent, hygroscopic agent and inorganic fine particles may be contained as required as long as the object of the present invention is not damaged.

The above multifilament may be produced, for example, by the following production process. That is, for example, the above polyester having an intrinsic viscosity of 0.55 to 0.80 is spun by a commonly used method, taken up as undrawn yarn (intermediate oriented yarn) at a rate of 2,000 to 4,300 m/min and drawn, or drawn before it is taken up to obtain the above multifilament.

Alternatively, the intermediate oriented yarn may be heated in a relaxed state (overfeed of 1.5 to 10%) by using a heater heated at 180 to 200° C. to obtain undrawn yarn (intermediate oriented yarn) having self-expansibility) under heating. Further, it may be subjected to false-twist crimping finish, air finish or twisting.

In the present invention, the woven fabric contains the above multifilament. The woven fabric contains preferably not less than 50 wt % (more preferably not less than 80 wt %) of the above multifilament. Particularly preferably, the woven fabric is composed of only the above multifilament.

In the above woven fabric, air permeability is preferably not more than 1.0 cc/cm²·sec (more preferably 0.1 to 1.0 cc/cm²·sec). When the air permeability is higher than 1.0 cc/cm²·sec, the inner material may protrude, or heat storage performance may be impaired.

To obtain a woven fabric having low air permeability, the cover factor CF defined by the following equation of the woven fabric is preferably set to not less than 1,200 (more preferably 1,300 to 2,500).

$$CF=(DWp/1.1)^{1/2} \times MWp+(DWf/1.1)^{1/2} \times MWf$$

[DWp is the total fineness (dtex) of warps, MWp is the weaving density of warps (number of warps/2.54 cm), DWf is the total fineness (dtex) of wefts, and MWf is the weaving density of wefts (number of wefts/2.54 cm)]

The weave of the woven fabric is not particularly limited and examples thereof include three foundation weaves such as plain weave, twill weave and sateen weave, derivative weaves such as derivative weave and derivative twill weave, single-backed double weaves such as warp double weave and weft double weave, warp velvet and rip-stop weave. Out of these, rip-stop weave is preferred from the viewpoint of tearing strength. The number of layers may be one, or two or more. As a weaving method, a commonly used method using an ordinary loom (for example, an ordinary water jet loom or air jet loom) may be employed.

When the woven fabric is subjected to calender finish and/or water absorption finish, low air permeability is further improved due to a small space between textures, thereby making it possible to absorb vapor and sweat generated from a human during exercise or sleeping advantageously. For the water absorption finish, for example, a method in which 5% owf of a hydrophilic agent (SR-1000 of Takamatsu Oil & Fat Co., Ltd.) is used to carry out water absorption finish at the same time as ordinary dyeing finish at 130° C. for 30 minutes in a method of providing a hydrophilic agent is effective but the present invention is not limited thereto.

As for preferred calender finish conditions, the temperature is preferably 130° C. or higher (more preferably 140 to 195° C.) and the linear pressure is preferably 200 to 20,000 N/cm.

Further, dyeing finish by a commonly used method, water-repellent finish, napping finish, various finishes for providing the functions of an ultraviolet screening or antistatic agent, antibacterial agent, deodorant, insect repellent, luminescent agent, retroreflective agent and minus ion generating agent, buffing finish and brushing finish may be additionally applied.

The weight of the woven fabric is preferably not more than 100 g/m² (more preferably 30 to 80 g/m²). It is more preferred that the weight should be smaller from the viewpoint of lightweight. However, when the weight is too small, water absorption performance may deteriorate. Therefore, the weight is preferably 30 to 80 g/m².

The ticking of the present invention is composed of the above woven fabric. At this point, it may be sewed, decorated or provided with an accessory.

Since the ticking of the present invention is excellent in flexibility, it is advantageously used as ticking for down jackets, jackets stuffed with inner cotton, sports-wears, outdoor wears, working clothing, protective clothing, heavy winter clothing, sleeping bags, cushions, quilt coverlets for a kotatsu and futons. It is particularly preferably used as futon ticking.

EXAMPLES

The following examples and comparative examples are provided for the purpose of further illustrating the present invention but are in no way to be taken as limiting. Measurement items in the examples were measured by the following methods.

(1) Areal Weight

This was measured in accordance with JISL1096 6.4.

(2) Air Permeability

Air permeability (cc/cm²·sec) was measured by the JISL1096 6.27 1 A method (Frazier method).

(3) Cover Factor CF of Woven Fabric

The cover factor CF of the woven fabric was calculated from the following equation.

$$CF=(DWp/1.1)^{1/2} \times MWp+(DWf/1.1)^{1/2} \times MWf$$

[DWp is the total fineness (dtex) of warps, MWp is the weaving density of warps (number of warps/2.54 cm), DWf is the total fineness (dtex) of wefts, and MWf is the weaving density of wefts (number of wefts/2.54 cm)]

(4) Flexibility of Ticking

This was evaluated by an examiner based on the following criteria.

Grade 3: excellent flexibility
Grade 2: moderate flexibility
Grade 1: poor flexibility Example 1

Polyethylene terephthalate multifilament drawn yarn (total fineness of 30 dtex/144 fil) was used as warp and weft to weave a known rip-stop texture material. This woven fabric was subjected to normal dyeing finish (dyed blue with a dispersion dye) and water absorption finish and then to final setting and calender finish to produce ticking. The water absorption finish was carried out with the following agent at 130° C. for 30 minutes at the same time as dyeing finish. The calender finish was carried out at a roll temperature of 160° C.

<Finish Agent Composition>

5% owf of water absorbing agent (5 wt % based on the weight of the fiber) (SR-1000 of Takamatsu oil & Fat Co., Ltd.) 95.0 wt % of water The obtained woven fabric for ticking had a weight of 57 gr/m², a CF of 1,760 and excellent flexibility (grade 3). The air permeability was 0.4 cc/cm²·sec.

When a futon was obtained by using the ticking as futon ticking, it had excellent flexibility.

Comparative Example 1

The procedure of Example 1 was repeated except that polyethylene terephthalate multifilament drawn yarn (total fineness of 56 dtex/72 fil) was used. The obtained ticking was inferior in flexibility (grade 1).

Effect of the Invention

According to the present invention, ticking having excellent flexibility is obtained.

INDUSTRIAL FEASIBILITY

According to the present invention, there is provided ticking having excellent flexibility which has great industrial value.

The invention claimed is:

1. A futon ticking composed of a woven fabric consisting of a polyester multifilament having a monofilament fineness of not more than 0.5 dtex, the number of filaments of 144 or more and a total fineness of not more than 50 dtex,
wherein a weight of the woven fabric is 30 to 80 g/m$^2$,
wherein an air permeability of the woven fabric is not more than 1.0 cc/cm$^2$·sec,
wherein a cover factor CF defined by the following equation of the woven fabric is not less than 1,200, $$CF=(DWp/1.1)^{1/2} \times MWp+(DWf/1.1)^{1/2} \times MWf$$

[DWp is the total fineness (dtex) of warps, MWp is the weaving density of warps (number of warps/2.54 cm), DWf is the total fineness (dtex) of wefts, and MWf is the weaving density of wefts (number of wefts/2.54 cm)].

2. The ticking according to claim 1, wherein the woven fabric is subjected to water absorption finish and/or calender finish.

\* \* \* \* \*